United States Patent [19]

Niwa et al.

[11] 3,956,337

[45] May 11, 1976

[54] PROCESS FOR THE PREPARATION OF D-GLUCONIC-δ-LACTAM

[75] Inventors: Tomizo Niwa, Yokohama; Takashi Tsuruoka, Kawasaki; Takashi Shomura; Shigeharu Inouye, both of Yokohama; Kazuo Saito, Fujisawa; Taro Niida, Yokohama, all of Japan

[73] Assignee: Meiji Seika Kaisha, Ltd., Tokyo, Japan

[22] Filed: Sept. 24, 1974

[21] Appl. No.: 508,734

[30] Foreign Application Priority Data

Sept. 25, 1973 Japan.............................. 48-106928

[52] U.S. Cl. .......................................... 260/293.86
[51] Int. Cl.² ..................................... C07D 211/74
[58] Field of Search .............................. 260/293.86

[56] References Cited
OTHER PUBLICATIONS

Inouye et al., Tetrahedron 24, 2125–2144 (1968).

Chem. Abstracts 42: 5929e (1948).

Chem. Abstracts 45:4755c (1951).

Dixon, "Enzymes," Academic Press, New York, (1958), p. 287.

Chem. Abstracts 49: 9709i (1955).

Boyer et al., "Enzymes, 2nd Ed.," Academic Press, New York, (1963), pp. 571–572.

Primary Examiner—G. Thomas Todd
Attorney, Agent, or Firm—Oblon, Fisher, Spivak, McClelland & Maier

[57] ABSTRACT

D-Gluconic-δ-lactam is obtained by oxidizing nojirimycin with glucose-oxidizing enzymes or by the action of microorganisms capable of producing glucose-oxidizing enzymes.

4 Claims, No Drawings

PROCESS FOR THE PREPARATION OF D-GLUCONIC-Δ-LACTAM

BACKGROUND OF THE INVENTION

1. Field of the Invention

The present invention relates to a process for the preparation of D-gluconic-δ-lactam with the formula: $C_6H_{11}O_5N$,

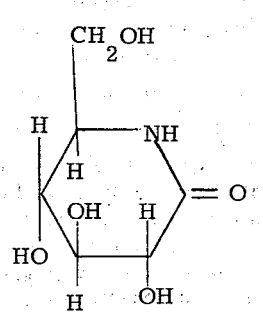

from the antibiotic substance, nojirimycin. Nojirimycin, which is used as a starting material in the process of the present invention, is an antibiotic which is obtained from the culture broth of a certain species of *Streptomyces* (T. Niida, et al, J. Antibiotics, Ser. A 20, 62, 1967). The chemical structure of Nojirimycin has been determined as 5-amino-5-deoxy-D-glucopyranose (S. Inouye, et al, Tetrahedron, 24, 2125, 1968). D-Gluconic-δ-lactam not only serves as a powerful competitive inhibitor for β-glucosidase (Agricultural and Biological Chemistry, Vol. 34, page 966, 1970) but also is an intermediate which is useful for the synthesis of various kinds of biologically and physiologically active substances (Japanese Pat. Application Nos. 78387/1973 and 76577/1973).

2. Description of the Prior Art

Procedures are known for the chemical oxidation of nojirimycin into D-gluconic-δ-lactam. For example, nojirimycin has been oxidized with hypoiodic acid (Tetrahedron, 24, page 2125, 1968) and hypobromic acid. However, when these methods are applied on an industrial scale to the preparation of D-gluconic-δ-lactam, the process inherently requires the handling of large amounts of iodine or bromine which are harmful to the human body. The use of such large amounts of halogen materials has the disadvantage of presenting environmental pollution problems.

A need, therefore, continues to exist for a method of oxidizing nojirimycin which does not present pollution problems and which avoids the necessity of using large amounts of halogen materials.

SUMMARY OF THE INVENTION

Accordingly, one object of the present invention is to provide a new method for the preparation of D-gluconic-δ-lactam.

Briefly, this object and other objects of the invention as hereinafter will become more readily apparent can be attained by a process for preparing D-gluconic-δ-lactam by oxidizing 5-amino-5-deoxy-D-glucose with glucose-oxidizing enzyme or by the action of a microorganism capable of producing glucose-oxidizing enzyme.

DETAILED DESCRIPTION OF THE PREFERRED EMBODIMENTS

The present process has evolved from the discovery that D-gluconic-δ-lactam can be readily obtained by the enzymatic oxidation of nojirimycin with glucose-oxidizing enzymes, or microorganisms producing a glucose oxidizing enzyme.

Though it has been assumed that nojirimycin acts as an inhibitor for glucose oxidase since there is a close similarity between nojirimycin and glucose in molecular structure, nojirimycin, contrary to expectation, is oxidized as the substrate by glucose oxidase into D-gluconic-δ-lactam.

Suitable glucose-oxidizing enzymes include glucose oxidase and glucose dehydrogenase. The former includes for example, deoxin, a commercially available crude enzyme preparation (produced by Nagase Sangyo Co./Japan) which is extracted from a culture broth of *Penicillium amagasakiensis*, a glucose oxidase preparation (produced by Miles Laboratory) which is extracted from *Aspergillus niger*, a crude enzyme which is obtained by extraction from *Penicillium notatum*, and the like. Nojirimycin can be oxidized without exception by enzymatic reaction of each of these glucose-oxidizing enzymes to produce D-gluconic-δ-lactam.

As a result of further studies concerning the production of the lactam, it has also been found that nojirimycin can be oxidized by the use of microorganisms which have the ability to produce glucose oxidizing enzyme to give D-gluconic-δ-lactam in higher yields. Suitable microorganisms capable of producing a glucose oxidizing enzyme include those which are employed for gluconic acid fermentation. In this case, the enzyme which takes part in the oxidation reaction is glucose dehydrogenase.

As is well known in the art, gluconic acid fermentation microorganisms exist widely in fungi and bacteria. Examples of the former include mold fungi such as Aspergillus, Penicillium and Rhizopus. Examples of the latter include Acetobacter, Gluconobacter and Pseudomonas.

In order to oxidize nojirimycin by any of these microorganisms, it is necessary to culture the microorganisms in a generally employed culture medium which contains sugars, proteins, amino acids and inorganic salts. Preferred culture media include those which contain glucose-buillon, sodium glutamate and inorganic salts. The culture temperature should be within the range of 20° to 37°C, and the culture time, though varying depending upon the culturing method which includes aeration, shaking and surface cultures, is preferably in the range of about 20 to 70 hours.

The harvested microorganisms were separated from the culture broth, followed preferably by washing with an inorganic or organic buffer solution. On the other hand, nojirimycin is preferably and practically dissolved in a suitable buffer solution, either neutral or weakly alkaline, in a concentration of 2 to 20%. The amount of cells added to the nojirimycin solution is ordinarily by wet weight, one-half to an amount equal to the weight of nojirimycin so as to facilitate the oxidation reaction at a relatively high rate. The oxidation reaction is preferably conducted at a temperature of 20° – 40°C with shaking or agitating. The reaction can be complete in a period of 1 to 24 hours. The harvested cells may be employed either wet or washed, or dry, or in a frozen and dried form. Moreover, the cells may be reused by separating them from the reaction system after completion of the reaction.

The process of the present invention using the bacterial or fungal cells to convert nojirimycin to D-gluconic-δ-lactam can be generally applied as it is to the process using the glucose-oxidizing enzymes or the crude enzyme for oxidizing nojirimycin to D-gluconic-δ-lactam. That is, an aqueous solution of nojirimycin can be mixed with a glucose-oxidizing enzyme or a crude preparation thereof with agitation at a pH of 5 to 8 under air-flowing conditions. The reaction temperature may generally be within a range of room temperature to about 60°, preferably 30° – 40°C. Though the reaction time may vary with the reaction temperatures employed, the reaction is ordinarily complete in a period of 10 to 80 hours.

In either case, the resulting reaction solution is then subjected to centrifugal separation, if necessary, to separate the cells or mycelia therefrom, and the thus separated solution is passed through a column filled with a strongly acidic ion exchange resin of, for example, Amberlite IR-120 ($H^+$ type) to remove unreacted nojirimycin therefrom. Thereafter, the solution is neutralized by passing the solution through a basic ion exchange resin of, for example, Amberlite Ir-45 ($OH^-$ type).

In the case when the oxidation reaction is effected at high efficiency, the neutralized solution is subjected as it is, to a condensation treatment to obtain crystals of D-gluconic-δ-lactam. However, if the neutralized solution contains some impurities, the same is purified by carbon chromatography or by other means, followed by condensation to yield crystals of the lactam. If desired, the lactam crystals may be further purified by a recrystallization process using a water-alcohol system.

D-Gluconic-δ-lactam is a suitable intermediate for the synthesis of β-glucuronidase inhibitor, D-glucaro-δ-lactam.

When oxygen gas is passed through an aqueous solution of D-gluconic-δ-lactam in the presence of a reduced platinum catalyst at a temperature of 65° – 70°C, while keeping the pH of the reaction mixture slightly alkaline, D-glucaro-δ-lactam is obtained which is fractionated and purified by chromatographic techniques.

D-glucaro-δ-lactam inhibits mouse liver β-glucuronidase by oral administration and rat serum β-glucuronidase by intraperitoneal administration. Furthermore, D-glucaro-δ-lactam alkyl esters have been found to be effective for adjuvant-arthritis of rats.

The table below shows the relative effectiveness for the treatment of adjuvant-arthritis in sprague-Dowly rats as estimated by th foot-volume in the right paw by the injection of 0.1 ml of killed mycelia of mycobacterium butyricum suspended in liquid paraffin (5.8 mg/ml).

The compounds to be tested were administered subcutaneously for 10 successive days and the curing effectiveness was estimated by the percent decrease of the initial volume 10 days after injection.

Table 1

| Compounds | Dose/day | Percent decrease of foot volume of adjuvant-arthritis |
|---|---|---|
| D-glucaro-δ-lactam methyl ester | 5 mg/kg | 28% |
| D-glucaro-δ-lactam ethyl ester | 5 mg/kg | 23% |
| Aspirin | 100 mg/kg | 26% |

Table 1-continued

| Compounds | Dose/day | Percent decrease of foot volume of adjuvant-arthritis |
|---|---|---|
| Untreated control | — | −7% |

Having generally described this invention, a further understanding can be obtained by reference to certain specific examples which are provided herein for purposes of illustration only and are not intended to be limiting unless otherwise specified.

EXAMPLE 1

*Pseudomonas ovalis* IFO 12051 was inoculated into 100 ml of sterile, 2% glucose bouillon culture medium in a 500 ml Sakaguchi flask, and cultured at 28°C for 42 hours while shaking the flask with a reciprocating shaker. Then, the harvested cells were isolated from the culture medium by centrifugal separation and dispersed in 50 ml of a M/20 phosphate buffer solution at pH 7.5, followed by centrifugation to obtain washed cells. A 0.9 g (by wet weight) amount of the washed cells was added to 50 ml of a 2% nojirimycin-phosphate buffer solution (M/20 at pH 7.5) for reaction at 28°C for 3.5 hours while shaking the reaction mixture with a reciprocating shaker, followed by centrifugal separation. The resulting supernatant solution was passed through a 15 ml column filled with Amberlite IR-120 ($H^+$ type), followed by neutralization using Amberlite IR-45 ($OH^-$ type). The neutralized liquid was condensed to about 5 ml under reduced pressure. The condensed solution was placed in an 85 ml carbon column and developed with water. Each 5 ml eluted fraction was subjected to paper partition chromatography, in which development was effected by an ascending method using Toyo filter paper No. 50 (Toyo Roshi Co./Japan) with a mixture of n-butanol, acetic acid and water in a ratio 3:1:1. The Rf value of D-gluconic-δ-lactam had been determined to be 0.3 to identify D-gluconic-δ-lactam, m.p. 203° – 205°C $[\alpha]_D = +63°$. The thus identified fractions were condensed under reduced pressure whereby 430 mg of crystals of the lactam were obtained.

EXAMPLE 2

A sterile culture medium with a pH value of 6.8 which contains 0.2% of sodium glutamate, 0.2% of $K_2HPO_4$, 0.01% of $MgCl_2$, 0.001% of $FeSO_4$, 2% of saccharose, 0.5% of peptone and 0.2% of yeast extract was inoculated with Gluconobacter suboxidans IAM 1829 (ATCC No. 621) by means of a platinum loop and was cultured at 28°C for 42 hours in a tube shaker. The thus obtained cultured cells were then inoculated in amounts of 1 ml in ten culture media (100 ml) of the same composition as mentioned above, which was sterilized and prepared in 500 ml Sakaguchi flasks. The inoculated cells were cultured at 28°C for 43 hours with a reciprocating shaker, followed by centrifugal separation and then washing with a phosphate buffer solution to obtain 5.5 g (wet weight) of the washed cells.

A 5 ml amount of a 2% nojirimycin solution having a pH of 7.5 and a concentration of M/20 and prepared with use of a phosphate buffer solution was placed in each of five Sakaguchi flasks, to which was added 0.9 g samples (wet weight) of the washed cells for reaction with the nojirimycin at 28°C for 3 hours by means of a reciprocating shaker. The resulting reaction solution was subjected to centrifugal sedimentation and then the resulting supernatant liquid was passed through a column of Amberlite IR-120 ($H^+$ type), followed by neutralization with Amberlite IR-45 ($OH^-$ type). The neutralized solution was condensed under reduced pressure and dried under a vacuum to yield 3.76 g of crystalline D-gluconic-δ-lactam.

EXAMPLE 3

*Aspergillus niger* IAM 2094, *Rhizopus delemer* IAM 6015 and *Gluconobacter suboxidans* ATCC No. 621 were, respectively, reacted with 1 g of nojirimycin in accordance with the process of Example 1 using the culture media of Example 1.

The yields of D-gluconic-δ-lactam are shown in Table 2.

Table 2

| Oxidation of nojirimycin by cells of some species of fungi and bacteria | | | |
|---|---|---|---|
| | Amount of Cells | Concentration of Nojirimycin | Yield of D-gluconic-δ-lactam |
| Aspergillus niger IAM 2094 | 1.1 g | 2.0% | 12.4% |
| Rhizopus delemer | 1.0 | 2.0% | 33.3 |
| Gluconobacter suboxidans ATCC No. 621 | 0.9 | 4.0 | 57.2 |
| Gluconobacter suboxidans ATCC No. 621 Reused | 0.8 | 2.0 | 22.0 |
| Frozen and Dried Cells of Gluconobacter suboxidans ATCC No. 621 | 0.2 | 2.0 | 49.1 |

EXAMPLE 4

A 300 g amount of nojirimycin was dissolved in 1.5 l of distilled water to which was added 80 g of deoxin-1, i.e., a crude powder of glucose oxidase with 10,000 units per mg which is produced by Penicillium amagasakiensis (produced by Nagase Sangyo Co./Japan). The pH of the reaction mixture was adjusted to 6.0 and then the reaction was conducted at 30°C in a 30 l jar fermenter with agitation at 300 r.p.m. under air-flowing conditions. After 65 hours of reaction, the reaction solution was passed through a column filled with Amberlite IR-120 ($H^+$ type, 1.5 l). The column was then washed with 7 l of water. The treated solution and the washings were combined (22 l), and the combined solution was then neutralized with Amberlite IR-45 ($OH^-$ type), followed by decolorization with 50 g of carbon powder. The decolorized solution was then condensed. To the condensed solution (500 ml) was added 100 ml of methanol, which was allowed to stand to cool in order to yield a crystalline product. The crystals were separated from the solution by filtration to give 220 g of D-gluconic-δ-lactam as needle-like white crystals (yield of 77%).

EXAMPLE 5

A 30 l liquid culture medium (adjusted pH to 7.0), which contained 2.0% starch, 2.5% soybean powder, 1.0% wheat germ, 0.5% peptone and 0.25% sodium chloride was inoculated with Penicillium notatum IFO 4640 in a jar fermenter. Culturing was conducted at 28°C for 72 hours with agitation under air-flowing conditions. After culturing, the resultant solution was subjected to filtration to yield 15 l of a filtrate. To the filtrate was added two volumes of cooled acetone, which was allowed to stand at 5°C. The resulting precipitate was separated by filtration from the solution. The separated precipitate was dissolved in 500 ml of water to remove insoluble matter from the solution by centrifugal separation. To the supernatant solution was added 10 g of nojirimycin for reaction at 35°C for 5 hours with agitation. The resulting reaction solution was treated in accordance with the procedure of Example 4 to yield 3.2 g of needle-like white crystals of D-gluconic-δ-lactam (yield of 32%).

Having now fully described this invention, it will be apparent to one of ordinary skill in the art that many changes and modifications can be made thereto without departing from the spirit or scope of the invention as set forth herein.

What is claimed as new and intended to be covered by Letters Patent is:

1. A process for the preparation of D-gluconic-δ-lactam, which comprises:
   oxidizing 5-amino-5-deoxy-D-glucose with glucose-oxidizing enzyme or by the action of a microorganism capable of producing glucose-oxidizing enzyme.

2. The process of claim 1, wherein the glucose-oxidizing enzyme is glucose dehydrogenase.

3. The process of claim 1, wherein the glucose-oxidizing enzyme is glucose oxidase.

4. The process of claim 1, wherein 5-amino-5-deoxy-D-glucose is oxidized by the action of cells of microorganisms selected from the group consisting of Pseudomonas, Gluconobacter, Aspergillus, Rhizopus, Penicillium and Acetobacter.

* * * * *